US011703365B2

(12) United States Patent
Tourchak et al.

(10) Patent No.: US 11,703,365 B2
(45) Date of Patent: Jul. 18, 2023

(54) AUTOMATIC FLUID FLOW SYSTEM WITH PUSH-BUTTON CONNECTION

(71) Applicant: C. R. Bard, Inc., Franklin Lakes, NJ (US)

(72) Inventors: Michal Tourchak, Atlanta, GA (US); Jason Jishen Cheng, Avondale Estates, GA (US); Rohit Sinha, Lawrenceville, GA (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 0 days.

(21) Appl. No.: 17/373,535

(22) Filed: Jul. 12, 2021

(65) Prior Publication Data

US 2022/0018692 A1 Jan. 20, 2022

Related U.S. Application Data

(60) Provisional application No. 63/051,760, filed on Jul. 14, 2020.

(51) Int. Cl.
*G01F 1/56* (2006.01)
*F16M 11/22* (2006.01)
*G01F 15/18* (2006.01)

(52) U.S. Cl.
CPC ............... *G01F 1/56* (2013.01); *F16M 11/22* (2013.01); *G01F 15/18* (2013.01); *F16M 2200/024* (2013.01)

(58) Field of Classification Search
CPC .. F16M 2200/024; F16M 11/22; G01F 15/18; G01F 1/56

(Continued)

(56) References Cited

U.S. PATENT DOCUMENTS 3,919,455 A 11/1975 Sigdell et al.
4,276,889 A 7/1981 Kuntz et al.
(Continued)

FOREIGN PATENT DOCUMENTS

CA 2882654 A1 10/2007
CN 2445749 Y 9/2001
(Continued)

OTHER PUBLICATIONS

PCT/US2019/045787 filed Aug. 8, 2019 International Preliminary Report on Patentability dated Feb. 16, 2021.

(Continued)

*Primary Examiner* — Nathaniel T Woodward
(74) *Attorney, Agent, or Firm* — Rutan & Tucker LLP

(57) ABSTRACT

Embodiments disclosed herein are directed to apparatus and methods for automatic fluid flow system connectors. The system generally includes a load cell interface coupled to a console and a ring connector coupled to a fluid collection system. The ring connector can be releasably engaged with the load cell using a push-button actuated locking mechanism. Embodiments of the locking mechanism can include a latch and aperture engagement, a shelf and ledge engagement, or a track and channel engagement, or combinations thereof. The ring connector and load cell can include electrical contacts configured to engage along an axis that extends perpendicular to a surface on which the electrical contacts are disposed. This is believed to reduce wear on the electrical contacts, thereby extending the usable life of the system.

27 Claims, 7 Drawing Sheets

(58) Field of Classification Search
USPC .......................................................... 73/861
See application file for complete search history.

(56) References Cited

U.S. PATENT DOCUMENTS

| | | |
|---|---|---|
| 4,286,590 A | 9/1981 | Murase |
| 4,291,692 A | 9/1981 | Bowman et al. |
| 4,296,749 A | 10/1981 | Pontifex |
| 4,305,405 A | 12/1981 | Meisch |
| 4,312,352 A | 1/1982 | Meisch et al. |
| 4,343,316 A | 8/1982 | Jespersen |
| 4,443,219 A | 4/1984 | Meisch et al. |
| 4,448,207 A | 5/1984 | Parrish |
| 4,509,366 A | 4/1985 | Matsushita et al. |
| 4,532,936 A | 8/1985 | LeVeen et al. |
| 4,658,834 A | 4/1987 | Blankenship et al. |
| 4,723,950 A | 2/1988 | Lee |
| 4,834,706 A | 5/1989 | Beck et al. |
| 4,850,375 A | 7/1989 | Rosenberg |
| 4,889,532 A | 12/1989 | Metz et al. |
| 5,002,541 A | 3/1991 | Conkling et al. |
| 5,409,014 A | 4/1995 | Napoli et al. |
| 5,725,515 A | 3/1998 | Propp |
| 5,733,319 A | 3/1998 | Neilson et al. |
| 5,747,824 A | 5/1998 | Jung et al. |
| 5,769,087 A | 6/1998 | Westphal et al. |
| 5,807,278 A | 9/1998 | McRae |
| 5,823,972 A | 10/1998 | McRae |
| 5,891,051 A | 4/1999 | Han et al. |
| 5,911,786 A | 6/1999 | Nielsen et al. |
| 6,129,684 A | 10/2000 | Sippel et al. |
| 6,132,407 A | 10/2000 | Genese et al. |
| 6,250,152 B1 | 6/2001 | Klein et al. |
| 6,261,254 B1 | 7/2001 | Baron et al. |
| 6,434,418 B1 | 8/2002 | Neal et al. |
| 6,592,612 B1 | 7/2003 | Samson et al. |
| 6,709,420 B1 | 3/2004 | Lincoln et al. |
| 6,716,200 B2 | 4/2004 | Bracken et al. |
| 7,011,634 B2 | 3/2006 | Paasch et al. |
| 7,437,945 B1 | 10/2008 | Feller |
| 7,442,754 B2 | 10/2008 | Tepper et al. |
| 7,739,907 B2 | 6/2010 | Boiarski |
| 7,871,385 B2 | 1/2011 | Levinson |
| 7,931,630 B2 | 4/2011 | Nishtala et al. |
| 7,998,126 B1 | 8/2011 | Fernandez |
| 8,328,733 B2 | 12/2012 | Forte et al. |
| 8,328,734 B2 | 12/2012 | Salvadori et al. |
| 8,337,476 B2 | 12/2012 | Greenwald et al. |
| 8,403,884 B2 | 3/2013 | Nishtala |
| 8,471,231 B2 | 6/2013 | Paz |
| 8,663,128 B2 | 3/2014 | Paz et al. |
| 8,773,259 B2 | 7/2014 | Judy et al. |
| 8,790,277 B2 | 7/2014 | Elliott et al. |
| 8,790,320 B2 | 7/2014 | Christensen |
| 8,790,577 B2 | 7/2014 | Mizumoto et al. |
| 8,813,551 B2 | 8/2014 | Boiarski |
| 8,827,924 B2 | 9/2014 | Paz et al. |
| 8,832,558 B2 | 9/2014 | Cardarelli et al. |
| 8,900,196 B2 | 12/2014 | Andino |
| 9,050,046 B2 | 6/2015 | Elliott et al. |
| 9,074,920 B2 | 7/2015 | Mendels et al. |
| 9,216,242 B2 | 12/2015 | Nishtala et al. |
| 9,480,821 B2 | 11/2016 | Ciccone et al. |
| 9,642,987 B2 | 5/2017 | Bierman et al. |
| 9,731,097 B2 | 8/2017 | Andino et al. |
| 9,895,095 B2 | 2/2018 | Chen |
| 10,182,747 B2 | 1/2019 | Charlez et al. |
| 10,245,008 B2 | 4/2019 | Paige |
| 10,362,981 B2 | 7/2019 | Paz et al. |
| 10,448,875 B2 | 10/2019 | Holt et al. |
| 2001/0056226 A1 | 12/2001 | Zodnik et al. |
| 2002/0161314 A1 | 10/2002 | Sarajarvi |
| 2002/0193760 A1 | 12/2002 | Thompson |
| 2003/0000303 A1 | 1/2003 | Livingston et al. |
| 2003/0163183 A1 | 8/2003 | Carson |
| 2003/0163287 A1 | 8/2003 | Vock et al. |
| 2004/0267086 A1 | 12/2004 | Anstadt et al. |
| 2005/0020958 A1 | 1/2005 | Paolini et al. |
| 2005/0065583 A1 | 3/2005 | Voorhees et al. |
| 2005/0172712 A1 | 8/2005 | Nyce |
| 2005/0247121 A1 | 11/2005 | Pelster |
| 2006/0100743 A1 | 5/2006 | Townsend et al. |
| 2007/0010797 A1 | 1/2007 | Nishtala et al. |
| 2007/0145137 A1 | 6/2007 | Mrowiec |
| 2007/0252714 A1 | 11/2007 | Rondoni et al. |
| 2009/0056020 A1 | 3/2009 | Caminade et al. |
| 2009/0099629 A1 | 4/2009 | Carson et al. |
| 2009/0157430 A1 | 6/2009 | Rule et al. |
| 2009/0287170 A1 | 11/2009 | Otto |
| 2009/0315684 A1 | 12/2009 | Sacco et al. |
| 2010/0094204 A1 | 4/2010 | Nishtala |
| 2010/0130949 A1 | 5/2010 | Garcia |
| 2010/0137743 A1 | 6/2010 | Nishtala et al. |
| 2011/0120219 A1 | 5/2011 | Barlesi et al. |
| 2011/0178425 A1 | 7/2011 | Nishtala et al. |
| 2011/0238042 A1 | 9/2011 | Davis et al. |
| 2011/0251572 A1 | 10/2011 | Nishtala et al. |
| 2011/0263952 A1 | 10/2011 | Bergman et al. |
| 2012/0029408 A1 | 2/2012 | Beaudin |
| 2012/0059286 A1 | 3/2012 | Hastings et al. |
| 2012/0078137 A1 | 3/2012 | Mendels et al. |
| 2012/0078235 A1 | 3/2012 | Martin et al. |
| 2012/0095304 A1 | 4/2012 | Biondi |
| 2012/0109008 A1 | 5/2012 | Charlez et al. |
| 2012/0123233 A1 | 5/2012 | Cohen |
| 2012/0127103 A1 | 5/2012 | Qualey et al. |
| 2012/0226196 A1 | 9/2012 | DiMino et al. |
| 2012/0302917 A1 | 11/2012 | Fitzgerald et al. |
| 2012/0323502 A1 | 12/2012 | Tanoura et al. |
| 2013/0066166 A1 | 3/2013 | Burnett et al. |
| 2013/0109927 A1 | 5/2013 | Menzel |
| 2013/0109928 A1 | 5/2013 | Menzel |
| 2013/0131610 A1 | 5/2013 | Dewaele et al. |
| 2013/0218106 A1 | 8/2013 | Coston et al. |
| 2013/0245498 A1 | 9/2013 | Delaney et al. |
| 2013/0267871 A1 | 10/2013 | Delaney et al. |
| 2014/0039348 A1 | 2/2014 | Bullington et al. |
| 2014/0155781 A1 | 6/2014 | Bullington et al. |
| 2014/0155782 A1 | 6/2014 | Bullington et al. |
| 2014/0159921 A1 | 6/2014 | Qualey et al. |
| 2014/0207085 A1 | 7/2014 | Brandt et al. |
| 2015/0343173 A1 | 12/2015 | Tobescu et al. |
| 2015/0359522 A1 | 12/2015 | Recht et al. |
| 2015/0362351 A1 | 12/2015 | Joshi et al. |
| 2016/0051176 A1 | 2/2016 | Ramos et al. |
| 2016/0183819 A1 | 6/2016 | Burnett et al. |
| 2017/0100068 A1 | 4/2017 | Kostov |
| 2017/0196478 A1 | 7/2017 | Hunter |
| 2017/0202698 A1 | 7/2017 | Zani et al. |
| 2017/0291012 A1 | 10/2017 | Iglesias |
| 2017/0307423 A1* | 10/2017 | Pahwa .................. G01G 19/18 |
| 2018/0280236 A1 | 10/2018 | Ludin et al. |
| 2018/0344234 A1 | 12/2018 | McKinney et al. |
| 2019/0046102 A1* | 2/2019 | Kushnir .................. G01F 23/20 |
| 2019/0069830 A1 | 3/2019 | Holt et al. |
| 2019/0223844 A1 | 7/2019 | Aboagye et al. |
| 2019/0247236 A1 | 8/2019 | Sides et al. |
| 2019/0321588 A1 | 10/2019 | Burnett et al. |
| 2019/0328945 A1 | 10/2019 | Analytis et al. |
| 2019/0365308 A1 | 12/2019 | Laing et al. |
| 2020/0085378 A1 | 3/2020 | Burnett et al. |
| 2020/0289749 A1 | 9/2020 | Odashima et al. |
| 2021/0077007 A1 | 3/2021 | Jouret et al. |
| 2022/0026001 A1 | 1/2022 | Cheng et al. |
| 2022/0192564 A1 | 6/2022 | Kriscovich et al. |
| 2022/0192565 A1 | 6/2022 | Cheng et al. |
| 2022/0192566 A1 | 6/2022 | Cheng et al. |
| 2022/0193375 A1 | 6/2022 | Rehm et al. |
| 2022/0296140 A1 | 9/2022 | Nguyen et al. |
| 2022/0386917 A1 | 12/2022 | Mann et al. |
| 2023/0022547 A1 | 1/2023 | Cho et al. |
| 2023/0025333 A1 | 1/2023 | Patel et al. |
| 2023/0028966 A1 | 1/2023 | Franano |
| 2023/0035669 A1 | 2/2023 | Raja et al. |

(56) References Cited

U.S. PATENT DOCUMENTS

| | | |
|---|---|---|
| 2023/0040915 A1 | 2/2023 | Compton et al. |
| 2023/0058553 A1 | 2/2023 | Fallows et al. |
| 2023/0060232 A1 | 3/2023 | Patel et al. |
| 2023/0084476 A1 | 3/2023 | Robichaud et al. |

FOREIGN PATENT DOCUMENTS

| | | |
|---|---|---|
| CN | 200951235 Y | 9/2007 |
| CN | 201492414 U | 6/2010 |
| CN | 102647939 A | 8/2012 |
| CN | 112426156 A | 3/2021 |
| EP | 0342028 A2 | 11/1989 |
| GB | 2576743 A | 3/2020 |
| JP | S49-75171 A | 7/1974 |
| JP | S54-147066 A | 11/1979 |
| JP | S58-190719 A | 11/1983 |
| JP | S60-219517 A | 11/1985 |
| JP | H02-057240 B2 | 12/1990 |
| JP | H08-271301 A | 10/1996 |
| JP | H10-104041 A | 4/1998 |
| JP | 2007-303982 A | 11/2007 |
| JP | 2008-524618 A | 7/2008 |
| JP | 2009-068959 A | 4/2009 |
| JP | 2010-121950 A | 6/2010 |
| JP | 2010-530978 A | 9/2010 |
| JP | 2012-105947 A | 6/2012 |
| JP | 2012-225790 A | 11/2012 |
| WO | 2014/043650 A2 | 3/2014 |
| WO | 2014108690 A1 | 7/2014 |
| WO | 2014/135856 A1 | 9/2014 |
| WO | 2014/151068 A2 | 9/2014 |
| WO | 2014145971 A2 | 9/2014 |
| WO | 2015/105916 A1 | 7/2015 |
| WO | 2015/127390 A1 | 8/2015 |
| WO | 2017/023794 A1 | 2/2017 |
| WO | 2019/226697 A1 | 11/2019 |

OTHER PUBLICATIONS

PCT/US2019/045787 filed Aug. 8, 2019 International Search Report and Written Opinion dated Oct. 2, 2019.

Bard Medical, Criticore Disposables—Non I.C., 3 pages, www.bardmedical.com/producls/patienl-moniloring-,ystems/criticore®-system/criticore®-disposables-non-ic/ Jan. 30, 2015.

Bard Medical, Criticore Infection Control Disposables, 3 pages, www.bardmedical.com/patienl-moniloring-,ystems/criticore®-system/criticore®-infection-conlrol-disposables/ Jan. 30, 2015.

Bard Medical, Criticore Monitor, 11 pages, www.bardmedical.com/products/patient-monitoring-systems/criticore®-monitor/ Jan. 30, 2015.

Bard Medical, Urine Meiers, 3 pages, www.bardmedical.com/producls/urological-drainage/urine-collection/urinemeters/Jan. 30, 2015.

Biometrix, Urimetrix, 4 pages, www.biometrixmedical.com/Products/56/Urimetrix%E2%84%A2 Oct. 29, 2014.

Observe Medical, sippi, 3 pages, www.observemedical.com/products.html Oct. 29, 2014.

PCT/US19/33389 filed May 21, 2019 International Search Report and Written Opinion dated Aug. 2, 2019.

PCT/US2016/044835 filed Jul. 20, 2016 International Search Report and Written Opinion dated Dec. 16, 2016.

U.S. Appl. No. 17/054,493, filed Nov. 10, 2020 Final Office Action dated May 31, 2022.

U.S. Appl. No. 15/748,107, filed Jan. 26, 2018 Final Office Action dated Dec. 23, 2020.

U.S. Appl. No. 15/748,107, filed Jan. 26, 2018 Final Office Action dated Feb. 7, 2022.

U.S. Appl. No. 15/748,107, filed Jan. 26, 2018 Non-Final Office Action dated Sep. 3, 2021.

U.S. Appl. No. 15/748,107, filed Jan. 26, 2018 Non-Final Office Action dated Sep. 4, 2020.

U.S. Appl. No. 17/054,493, filed Nov. 10, 2020 Non-Final Office Action dated Nov. 24, 2021.

U.S. Appl. No. 15/748,107, filed Jan. 26, 2018 Notice of Allowance dated Dec. 12, 2022.

U.S. Appl. No. 17/054,493, filed Nov. 10, 2020 Non-Final Office Action dated Jan. 27, 2023.

U.S. Appl. No. 17/3026,821, filed May 3, 2021 Non-Final Office Action dated Jan. 10, 2023.

U.S. Appl. No. 17/262,080, filed Jan. 21, 2021 Non-Final Office Action dated Apr. 6, 2023.

\* cited by examiner

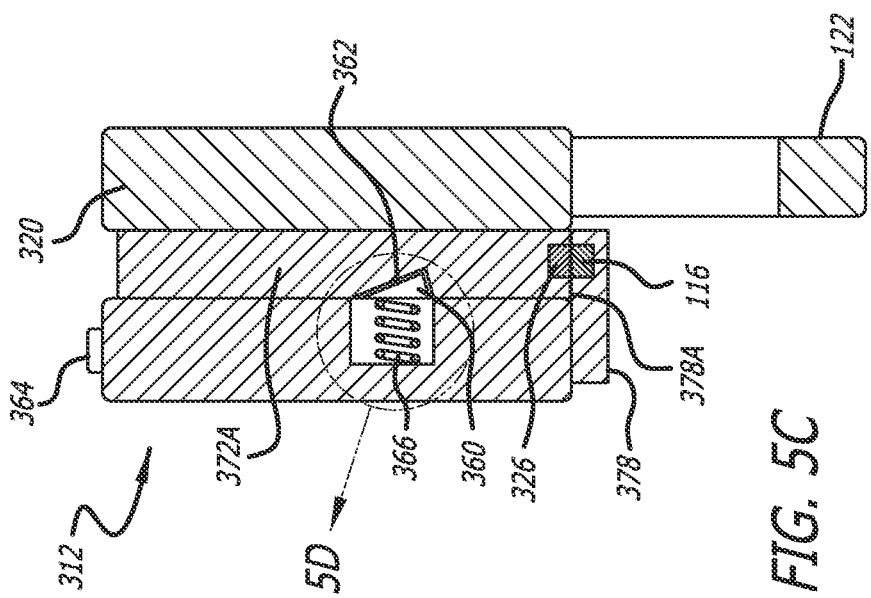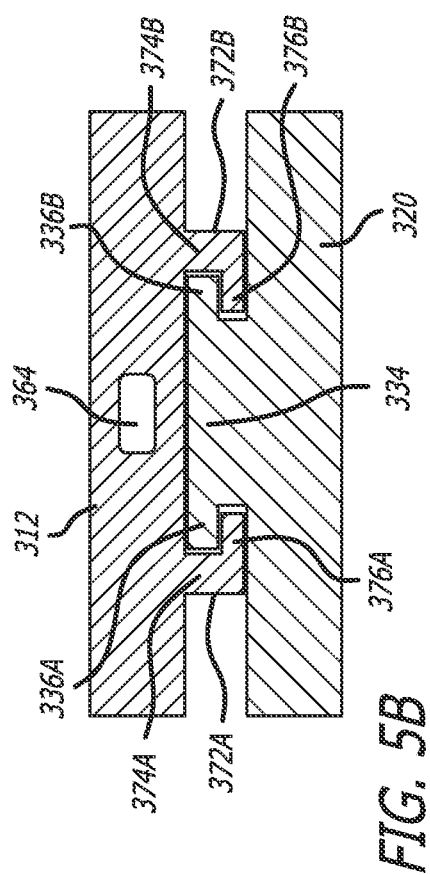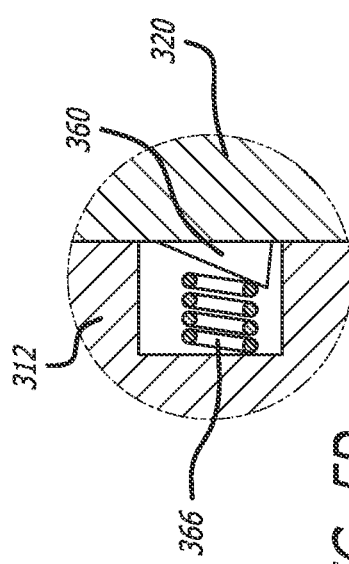

AUTOMATIC FLUID FLOW SYSTEM WITH PUSH-BUTTON CONNECTION

PRIORITY

This application claims the benefit of priority to U.S. Provisional Application No. 63/051,760, filed Jul. 14, 2020, which is incorporated by reference in its entirety into this application.

SUMMARY

Briefly summarized, embodiments disclosed herein are directed to automatic fluid flow system connectors and the like. In order to maintain a high accuracy of fluid flow monitoring, automatic fluid flow systems can determine a change in fluid volume by detecting a change in weight of a fluid collection system, over time. These detection systems rely on precise weight measurements to provide high accuracy of fluid flow in low-flow situations. As such, interface mechanisms configured to engage the fluid collection system with the automatic fluid flow system require a secure fit to ensure the downward forces, or changes thereof, are accurately transferred to the automatic fluid flow system. Further, the interface mechanisms must sustain repeated engagements and disengagements as different fluid collection systems are coupled or uncoupled to the automatic fluid flow system.

Disclosed herein is an automatic fluid flow measuring system including, a ring connector configured to be coupled to a fluid collection system and including a first electrical contact disposed on a first surface, and a load cell including a second electrical contact disposed on a second surface, the load cell configured to engage and retain the ring connector such that the first electrical contact engages the second electrical contact along an axis extending perpendicular to both the first surface and the second surface.

In some embodiments, one of the ring connector or the load cell includes a push-button actuator configured to releasably engage the load cell with the ring connector. In some embodiments, the load cell includes a carriage defining the push-button actuator and slidable between a locked configuration and an unlocked configuration. In some embodiments, the load cell includes a biasing member configured to bias the carriage towards the locked configuration. In some embodiments, the push-button actuator is configured to transition the carriage from the locked configuration to the unlocked configuration. In some embodiments, the carriage includes an aperture configured to receive a latch in the unlocked configuration and retain the latch in the locked configuration, the latch extending from a rear surface of the ring connector.

In some embodiments, a surface of the latch engages the load cell to transfer a force from the ring connector to the load cell. In some embodiments, the load cell includes a shelf extending horizontally across a portion of a front face of the load cell, and configured to engage the ring connector to receive a force from the ring connector to the load cell. In some embodiments, the load cell and the ring connector engage using a French cleat mechanism. In some embodiments, the load cell includes a first rail and a second rail defining a channel and configured to slidably engage a track in a first direction, the track extending from a rear surface of the ring connector. In some embodiments, the load cell includes a pawl configured to engage a recess disposed on the ring connector, the pawl configured to inhibit movement of the track within the channel in a second direction.

In some embodiments, the push-button actuator is configured to retract the pawl to allow movement of the track in the second direction. In some embodiments, the track defines a T-shaped horizontal cross-section and the channel is configured to slidably receive the track along a vertical axis. In some embodiments, the load cell includes a seat configured to engage the ring connector and to transfer a force from the ring connector to the load cell. In some embodiments, a lower surface of the ring connector defines the first surface and a top surface of the seat defines the second surface.

Also disclosed is a method of measuring a fluid flow including, actuating a push button actuator disposed on a load cell, the load cell configured to releasably engage a ring connector coupled to a fluid collection system, transitioning a carriage from a locked configuration to an unlocked configuration, urging a latch through an aperture of the carriage, the latch extending from a rear surface of the ring connector, transitioning the carriage from the unlocked configuration to the locked configuration to retain the latch within the aperture, detecting a force applied to the load cell by the ring connector to determine a fluid volume disposed within the fluid collection system, and detecting a change in the force over time to determine a fluid flow.

In some embodiments, the method further includes engaging a first electrical contact disposed on the ring connector, with a second electrical contact disposed on the load cell to communicatively couple the ring connector to the load cell. In some embodiments, the load cell includes a biasing member configured to bias the carriage to a locked configuration. In some embodiments, the load cell includes a shelf extending horizontally and configured to engage the ring connector to transfer a force from the ring connector to the load cell. In some embodiments, the load cell includes a French cleat configured to engage the ring connector to transfer a force from the ring connector to the load cell. In some embodiments, the ring connector includes logic configured to store one of fluid flow information, system information, or patient information thereon.

Also disclosed is a method of measuring a fluid volume including, providing a load cell including a channel configured to slidably engage a track extending from a ring connector, the ring connector coupled to a fluid collection system, sliding the track through the channel in a first direction until a surface of the ring connector engages a seat extending from the load cell, transferring a force from the ring connector to the load cell, and detecting a change in the force over time to determine a fluid flow.

In some embodiments, the method further includes engaging a first electrical contact disposed on the ring connector, with a second electrical contact disposed on the seat of the load cell, to communicatively couple the ring connector to the load cell. In some embodiments, the ring connector includes logic configured to store one of fluid flow information, system information, or patient information thereon. In some embodiments, the method further includes engaging a pawl, extending from the load cell, with a recess disposed on the ring connector to inhibit movement of the track through the channel in a second direction, opposite the first direction. In some embodiments, the method further includes actuating a push-button to retract the pawl from the recess to allow the track to slide through the channel in the second direction. In some embodiments, the load cell includes a biasing member configured to bias the pawl to an extending position.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIG. 5B shows a top view of a ring connector and a load cell interface, in accordance with embodiments disclosed herein.

FIG. 5C shows a side view of a ring connector and a load cell interface, in accordance with embodiments disclosed herein.

FIG. 5D shows close up detail of the ring connector and the load cell interface of FIG. 5C, in accordance with embodiments disclosed herein.

DESCRIPTION

Figure 1A:
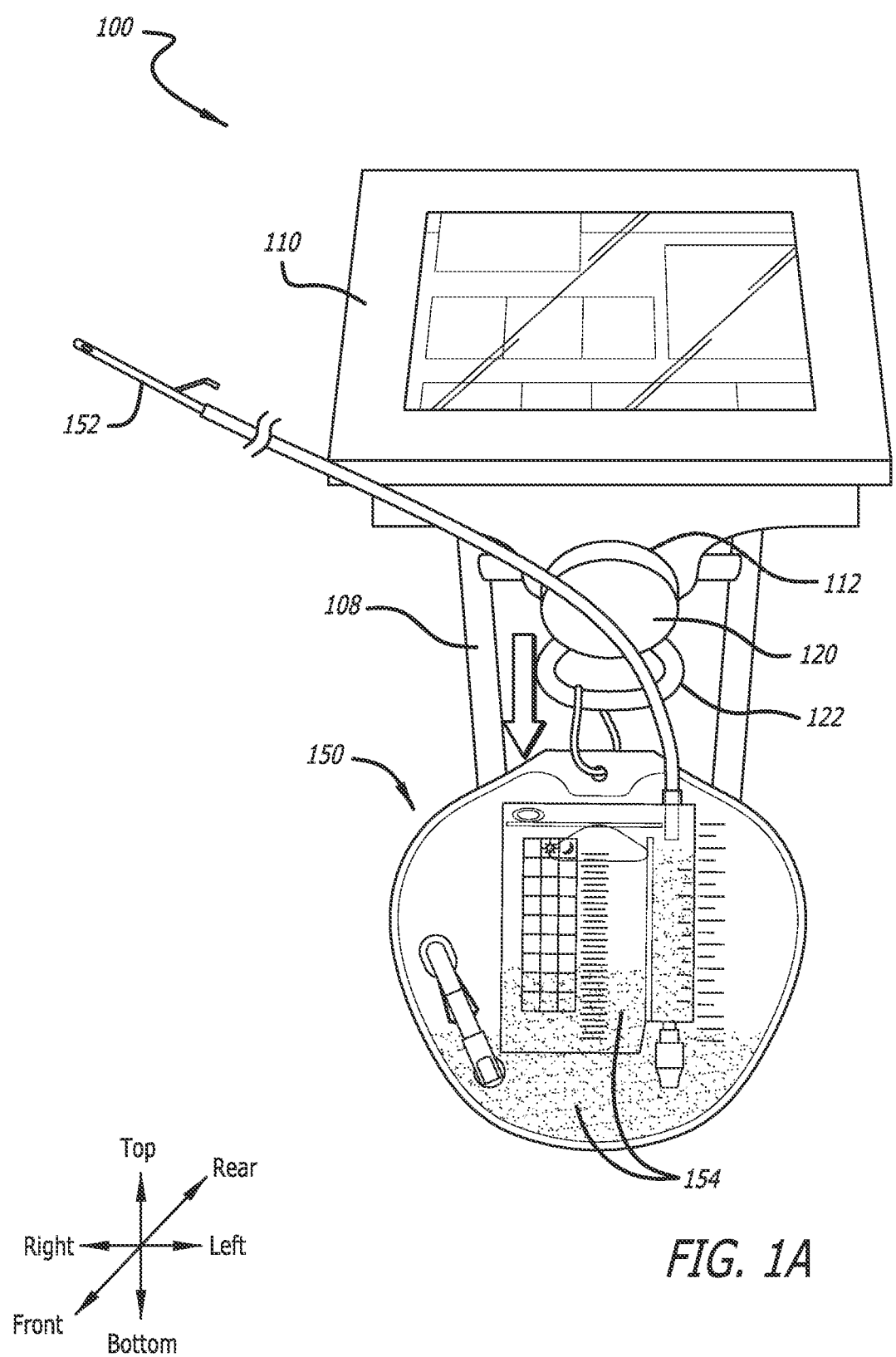
FIG. 1A shows a perspective view of an exemplary automatic fluid flow system including a fluid collection system, in accordance with embodiments disclosed herein.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Terminology

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Singular forms of "a," "an," and "the" include plural references unless the context clearly dictates otherwise.

In the following description, certain terminology is used to describe aspects of the invention. For example, in certain situations, the term "logic" is representative of hardware, firmware or software that is configured to perform one or more functions. As hardware, logic may include circuitry having data processing or storage functionality. Examples of such circuitry may include, but are not limited or restricted to a hardware processor (e.g., microprocessor with one or more processor cores, a digital signal processor, a programmable gate array, a microcontroller, an application specific integrated circuit "ASIC," etc.), a semiconductor memory, or combinatorial elements.

Alternatively, logic may be software, such as executable code in the form of an executable application, an Application Programming Interface (API), a subroutine, a function, a procedure, an applet, a servlet, a routine, source code, object code, a shared library/dynamic load library, or one or more instructions. The software may be stored in any type of a suitable non-transitory storage medium, or transitory storage medium (e.g., electrical, optical, acoustical or other form of propagated signals such as carrier waves, infrared signals, or digital signals). Examples of non-transitory storage medium may include, but are not limited or restricted to a programmable circuit; semiconductor memory; non-persistent storage such as volatile memory (e.g., any type of random access memory "RAM"); or persistent storage such as non-volatile memory (e.g., read-only memory "ROM," power-backed RAM, flash memory, phase-change memory, etc.), a solid-state drive, hard disk drive, an optical disc drive, or a portable memory device. As firmware, the executable code may be stored in persistent storage.

The term "computing device" should be construed as electronics with the data processing capability and/or a capability of connecting to any type of network, such as a public network (e.g., Internet), a private network (e.g., a wireless data telecommunication network, a local area network "LAN", etc.), or a combination of networks. Examples of a computing device may include, but are not limited or restricted to, the following: a server, an endpoint device (e.g., a laptop, a smartphone, a tablet, a "wearable" device such as a smart watch, augmented or virtual reality viewer, or the like, a desktop computer, a netbook, a medical device, or any general-purpose or special-purpose, user-controlled electronic device), a mainframe, internet server, a router; or the like.

A "message" generally refers to information transmitted in one or more electrical signals that collectively represent electrically stored data in a prescribed format. Each message may be in the form of one or more packets, frames, HTTP-based transmissions, or any other series of bits having the prescribed format.

The term "computerized" generally represents that any corresponding operations are conducted by hardware in combination with software and/or firmware.

Labels such as "left," "right," "upper", "lower," "top," "bottom," "front," "back," and the like are used for convenience and are not intended to imply, for example, any particular fixed location, orientation, or direction. Instead, such labels are used to reflect, for example, relative location, orientation, or directions. To assist in the description of embodiments described herein, the "top," "bottom," "left," "right," "front" and "back" directions are in reference to the orientation of the device as shown in FIG. 1A. A vertical axis extends between a top direction and a bottom direction. A lateral axis extends horizontally between a left direction and a right direction, substantially normal to the vertical axis. A transverse axis extends horizontally between a front direction and a back direction, substantially normal to both the vertical and lateral axes. A horizontal plane is defined by the lateral and transverse axes. A median plane is defined by the vertical and transverse axes. A frontal plane is defined by the vertical and lateral axes.

Unless defined otherwise, all technical and scientific terms used herein have the same meaning as commonly understood by those of ordinary skill in the art.

Figure 1C:
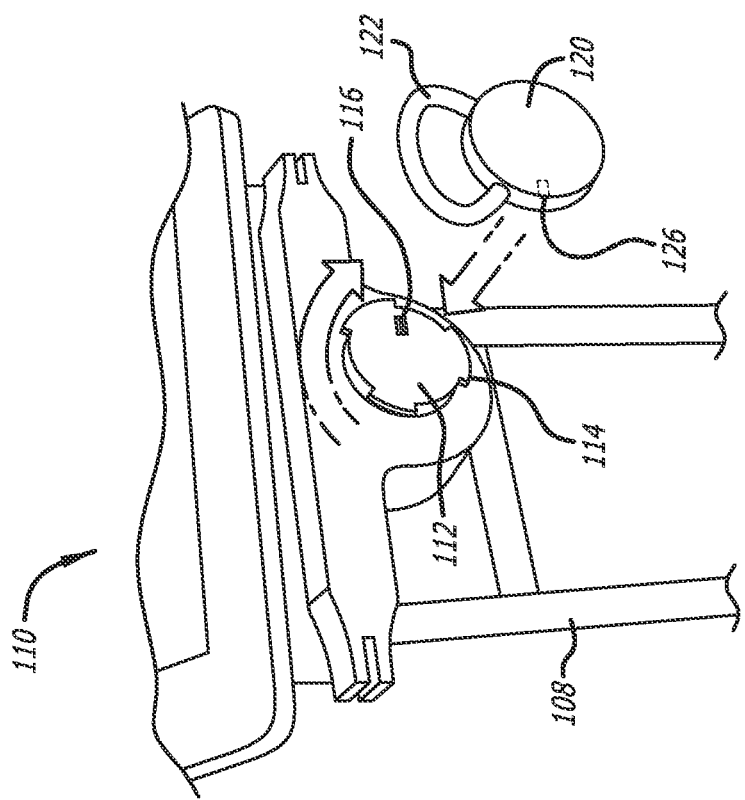
FIGS. 1B-1C show perspective views of a load cell interface and a ring connector of an exemplary automatic fluid flow system, in accordance with embodiments disclosed herein.
Figure 1B:
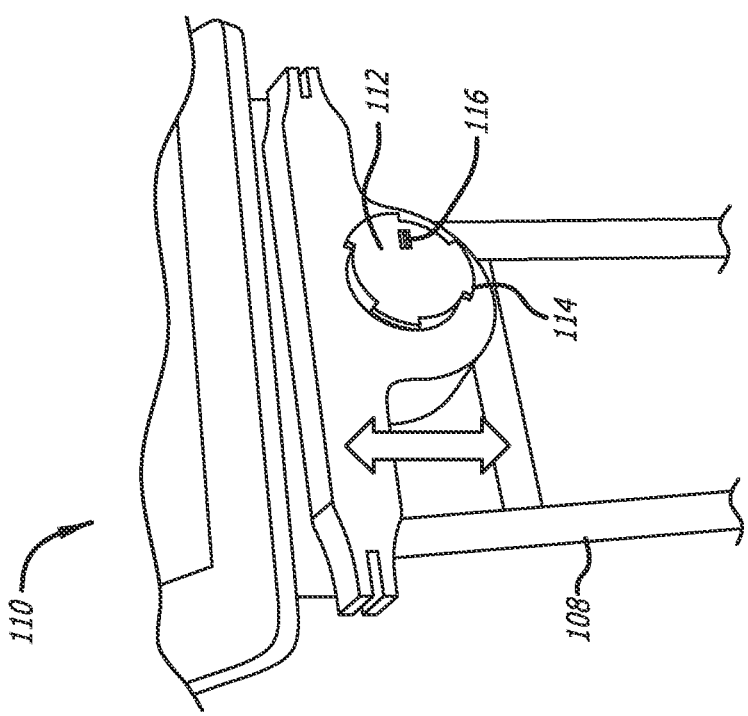

FIGS. 1A-1C show details of an exemplary automatic fluid flow measuring system ("system") 100 including a fluid collection system 150 coupled thereto, in accordance with embodiments disclosed herein. The automatic fluid flow system 100 generally includes a console 110 including a load cell interface ("load cell") 112 configured to engage a ring connector ("ring") 120. The ring connector 120 can include a loop 122, peg, hook, or similar structure from which a fluid collection system 150 can be suspended. The fluid collection system 150 can generally include one or more collection containers 154 in fluid communication with a catheter 152 or similar device configured to drain a fluid from a cavity of a patient. Optionally, the console 110 can be supported by a stand 108, or similar structure configured to support the console 110, ring 120, fluid collection system 150, and the like.

In an embodiment, the catheter 152 can be an internal catheter or an external catheter. Exemplary catheters can include external urinary catheter, internal urinary catheter, Foley catheter, balloon catheter, peritoneal catheters, or the like. Exemplary fluids collected can include urine, blood, peritoneal fluid, interstitial fluid, or the like. In an embodiment, the catheter 152 can be a Foley catheter configured to drain a fluid, e.g. urine, from a bladder of a patient.

As shown in FIG. 1B, the load cell interface 112 can be configured to detect a change in vertical movement relative to the console 110. In an embodiment, the load cell interface 112 can be configured to detect a force applied thereto, along an axis extending parallel to a front surface of the load cell 112, or perpendicular to a transverse axis of the load cell. For example, as shown in FIG. 1C, a ring connector 120 can be coupled to the load cell interface 112 by engaging the load cell 112 along the transverse axis. The ring connector 120 can then be locked to the load cell 112 by rotating the ring connector 120 about the transverse axis. In an embodiment, the ring connector 120 can be rotated between 5° and 360°. In an embodiment, the ring connector 120 can be rotated substantially 180°.

A fluid collection system 150 can then be coupled to the ring connector 120. A change in fluid volume within the fluid collection system 150, and thereby a change in weight thereof, causes a change in force applied to the load cell interface 112. The change in force can be substantially along a vertical axis, however it will be appreciated that the load cell interface 112 can detect force changes along other axes in three-dimensional space, as well.

The change in force applied to the load cell interface 112 can be detected by the console 110 to determine a change in fluid volume within the fluid collection system 150. This information can then be stored, analyzed, displayed, or communicated to one or more external computing devices or networks, e.g. an Electronic Health Record (EHR) system, network, or the like.

In an embodiment, the load cell interface 112 can include a locking mechanism 114 and an electrical contact interface 116. The locking mechanism 114 can be configured to engage a corresponding locking mechanism disposed on the ring connector 120 to secure the ring connector 120 to the load cell interface 112, as described in more detail herein. As noted, the locking mechanism 114 can be a rotational locking mechanism 114 where the ring connector 120 is rotated through a frontal plane by substantially 180° to transition the ring connector between a locked configuration (FIG. 1A) and an unlocked configuration (FIG. 1C).

In an embodiment, the electrical contact interface 116 can be configured to engage a corresponding electrical contact interface 126 disposed on the ring connector 120 to communicatively couple the ring connector 120 to the load cell interface 112 of the console 110. In an embodiment, the ring connector electrical contact interface 126 engages the load cell electrical contact interface 116 in one of the locked configuration or the unlocked configuration.

In an embodiment, the ring connector 120 can include one or more processors, memory, storage logic, communication logic, or the like, configured to store information and communicate with the console 110 by way of the ring connector electrical contact interface 126 and the load cell electrical contact interface 116. For example, the ring connector 120 can store fluid flow information, system information, patient information, or the like. Fluid flow information can include current or historical fluid volume information, fluid flow information (i.e. change in volume over time), combinations thereof or the like. System information can include the make, model, serial number, etc. of the ring connector 120, fluid collection system 150, the console 110, components thereof, or the like. Patient information can include height, weight, blood pressure, etc. of the patient, or similar health record information.

Advantageously, the fluid flow information, system information, patient information, and the like, can be stored to the ring connector 120 and transported with the collection system 150 and the patient. The ring connector 120 and collection system 150 assembly can then be coupled to a different console 110, e.g. during transport or console malfunction, and continue to measure fluid flow without losing the historical data, or transferring the data separately. As such, the data remains with the patient and the collection system 150 and is not lost.

Figure 2A:
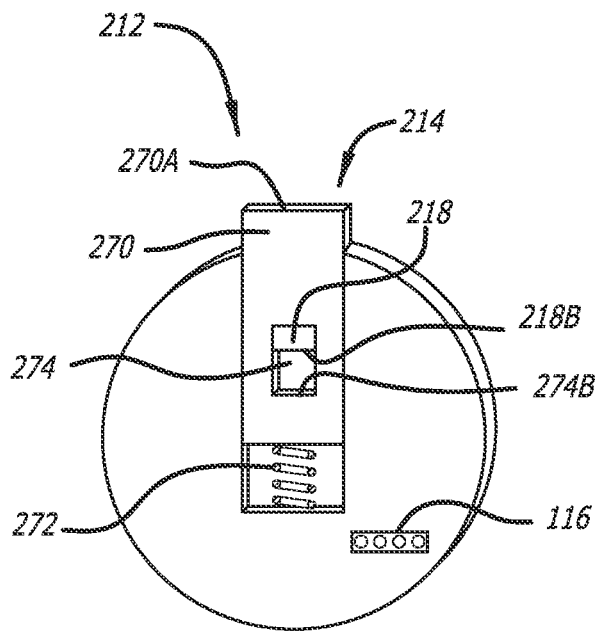
FIG. 2A shows a perspective view of a load cell interface in a locked position, in accordance with embodiments disclosed herein.
Figure 2B:
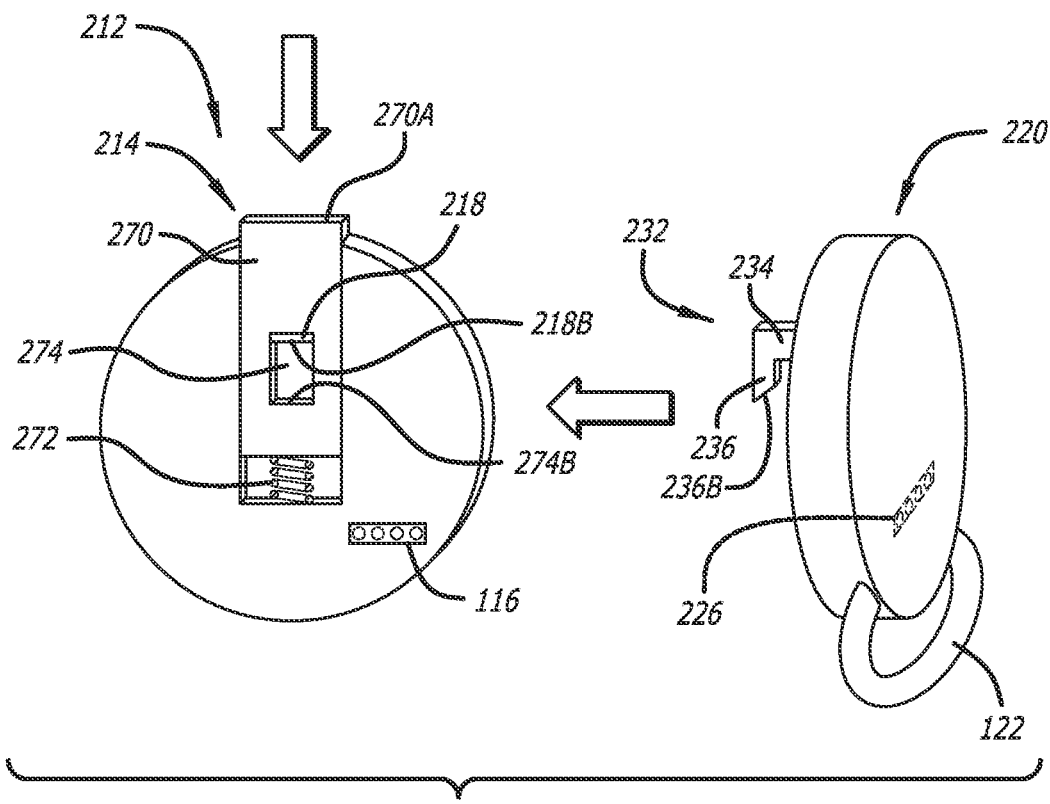
FIG. 2B shows a perspective view of a ring connector and a load cell interface in an unlocked position, in accordance with embodiments disclosed herein.
Figure 3A:
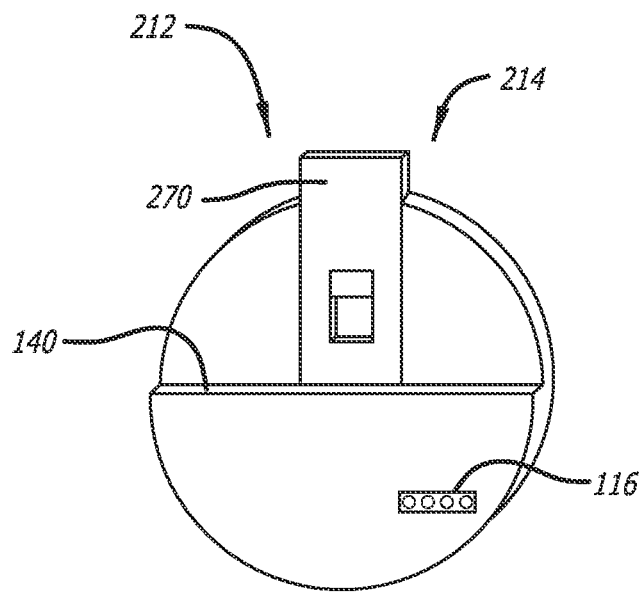
FIG. 3A shows a perspective view of a load cell interface in a locked position, in accordance with embodiments disclosed herein.
Figure 3B:
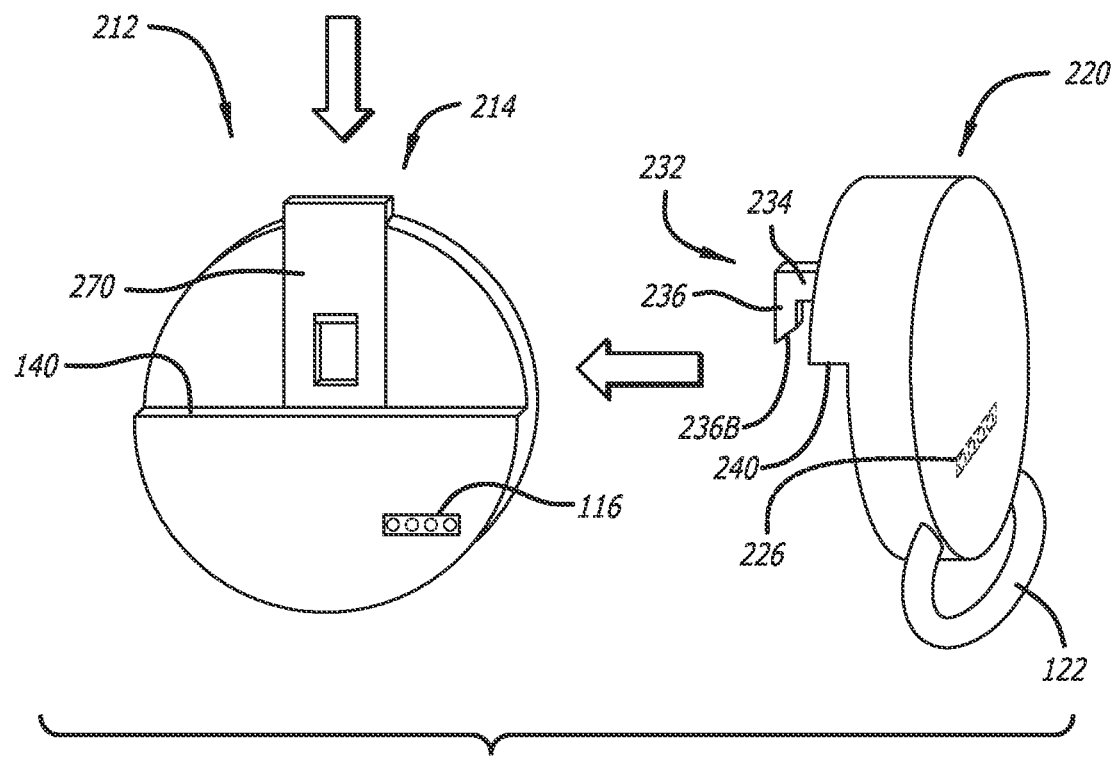
FIG. 3B shows a perspective view of a ring connector and a load cell interface in an unlocked position, in accordance with embodiments disclosed herein.

FIGS. 2A-4C show embodiments of a load cell interface 212 and a ring connector 220 including a push-button actuated locking mechanism 214 configured to releasably engage the ring connector 220 with the load cell 212. As shown in FIGS. 2A-2B, the push-button actuated locking mechanism 214 includes a carriage 270 transitionable between a closed, or locked, position as shown in FIG. 2A, and an open, or unlocked, position as shown in FIG. 2B. The carriage 270 can be slidably engaged with the load cell 212 along a vertical axis. A top surface 270A of the carriage 270 can extend to, or above, a surface of the load cell 212 and can define an actuator surface. The locking mechanism 214 can further include a biasing member 272, e.g. a compression spring, or the like, configured to bias the carriage 270 towards the closed or locked position (FIG. 2A).

The carriage 270 can further include an aperture 274 configured to receive a latch 232 therethrough, which extends from a rear surface of the ring connector 220. The latch 232 can include a "hook" shape, including a post 234 extending horizontally from a rear surface of the ring connector 220, and a flange 236 extending perpendicular from the post 234. Optionally, one of the post 234 or the flange 236 can include a chamfered edge to facilitate engagement with the aperture 274.

The load cell 212 further includes a block portion ("block") 218, extending across a portion of the aperture 274 and is arranged in a fixed relationship relative to the load cell 212. As the carriage 270 transitions along a vertical axis between the locked position and the unlocked position, a lower edge 274B of the aperture 274 travels away from the block 218 until, in the unlocked position, a distance between the lower edge 274B of the aperture 274 and a lower edge 218B of the block 218 is sufficient to allow ingress/egress of the latch 232 to/from the aperture 274.

In like manner, as the carriage 270 travels from the unlocked position to the locked position, a lower edge 274B of the aperture 274 travels toward the block 218 until, in the locked position, a distance between the lower edge 274B of the aperture 274 and a lower edge 218B of the block 218 inhibits ingress/egress of the latch 232 to/from the aperture 274. For example, a lower edge 274B of the aperture 274 engages the flange 236 and inhibits egress of the latch 232.

In an exemplary method of use, a user can depress the top surface 270A of the carriage 270 to overcome the force of the biasing member 272 and transition the locking mechanism 214 along a vertical axis from the locked position to the unlocked position. The ring connector 220 can then be urged horizontally until the hook 232 engages the aperture 274. The user can then release the carriage 270 to allow the biasing member 272 to transition the carriage 270 from the unlocked position to the locked position where a bottom surface 274B of the aperture engages the flange 236 to inhibit egress of the hook 232 from the aperture 274.

A surface of the latch 232, e.g. a lower surface 236B of the flange 236, can engage a surface of the load cell 212 to transfer any downward force from the fluid collection system 150 onto the load cell 212. For example, as a fluid volume within the fluid collection system 150 increases, the weight of the fluid collection system 150 also increases and applies a downward force on the loop 122 and ring connector 220. The hook 232 transfers the downward force to the load cell 212 which in turn is detected by the console 110. The console 110 can then determine an amount of fluid disposed within the fluid collection system 150 by a corresponding change in movement or pressure applied to the load cell 212. Similarly, the console 110 can determine a fluid flow by determining a change in fluid volume over time.

In an embodiment, the load cell 212 can include an electrical contact 116 disposed on a front surface thereof. The ring connector 220 can include an electrical contact 226 disposed on a rear surface and configured to align with the load cell electrical contact 116. In the locked configuration, the ring connector electrical contact 226 contacts the load cell electrical contact 116 to communicatively couple with ring connector 220 with the console 110, as described herein. Advantageously, the ring connector electrical contact 226 engages the load cell electrical contact 116 along an axis that extends perpendicular to the surfaces that the electrical contacts 116, 226 are disposed on. This mitigates wear on the electrical contact surfaces, providing a reliable communicative coupling therebetween and extends the usable life of the system 100.

FIGS. 3A-4C show an embodiment of a load cell 212 and a ring connector 220 that includes a push-button actuated locking mechanism 214, and further includes a shelf 140 configured to engage a ledge surface 240 extending from a rear surface of the ring connector 220. As described herein, the push-button actuated locking mechanism 214 can include a carriage 270 transitionable between an open or locked configuration (FIG. 3A) and a closed or an unlocked configuration (FIG. 3B) to retain a hook 232 extending from the ring connector 220. The load cell 212 can further include an electrical contact 116 configured to engage a ring connector electrical contact 226 when in the ring connector 220 is engaged therewith.

In an embodiment, the load cell 212 can further include a shelf 140 extending substantially horizontally from a front surface of the load cell 212. The shelf can be configured to engage a ledge 240 extending substantially horizontally from a rear surface of ring connector 220. Advantageously, the shelf 140 can engage the ledge 240 to support the ring connector 220 and the weight of the fluid collection system 150 coupled thereto. The downward force exerted by the ring connector 220 can be spread across a greater surface area to distribute the pressure applied. Advantageously this reduces the amount of pressure applied to the hook 232 and extends the longevity of the system 100.

Figure 4A:
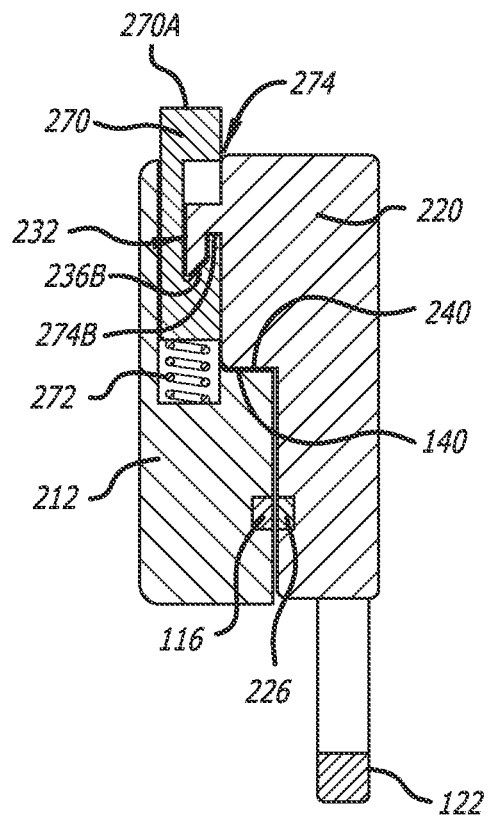
FIG. 4A shows a cross-sectional view of a ring connector and a load cell interface in a locked position, in accordance with embodiments disclosed herein.
Figure 4B:
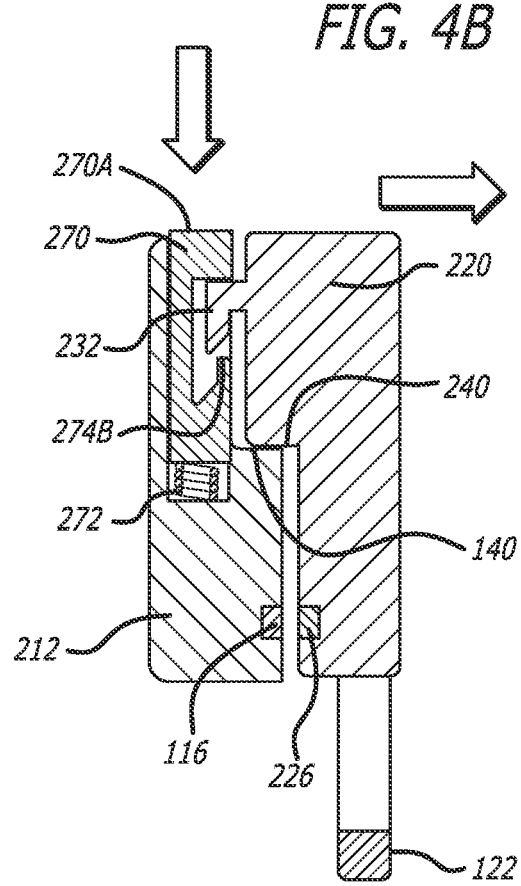
FIG. 4B shows a cross-sectional view of a ring connector and a load cell interface in an unlocked position, in accordance with embodiments disclosed herein.
Figure 4C:
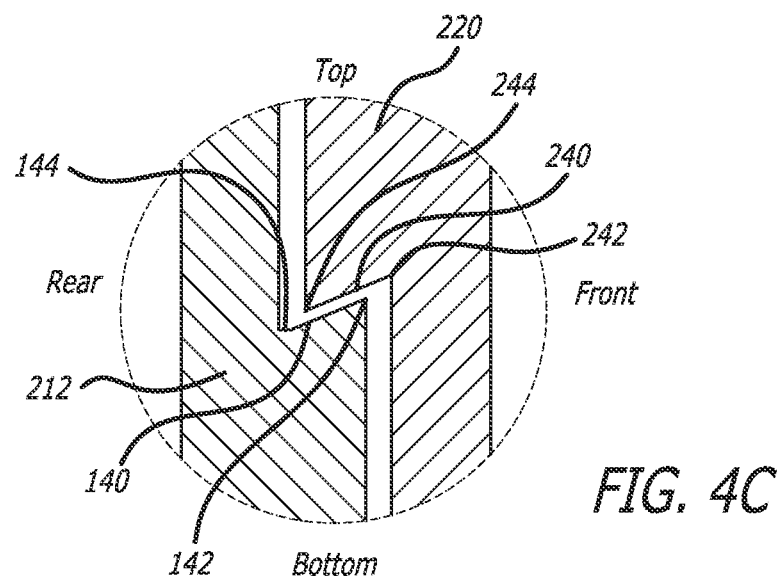
FIG. 4C shows close up detail of a ring connector and a load cell interface, in accordance with embodiments disclosed herein.
Figure 5A:
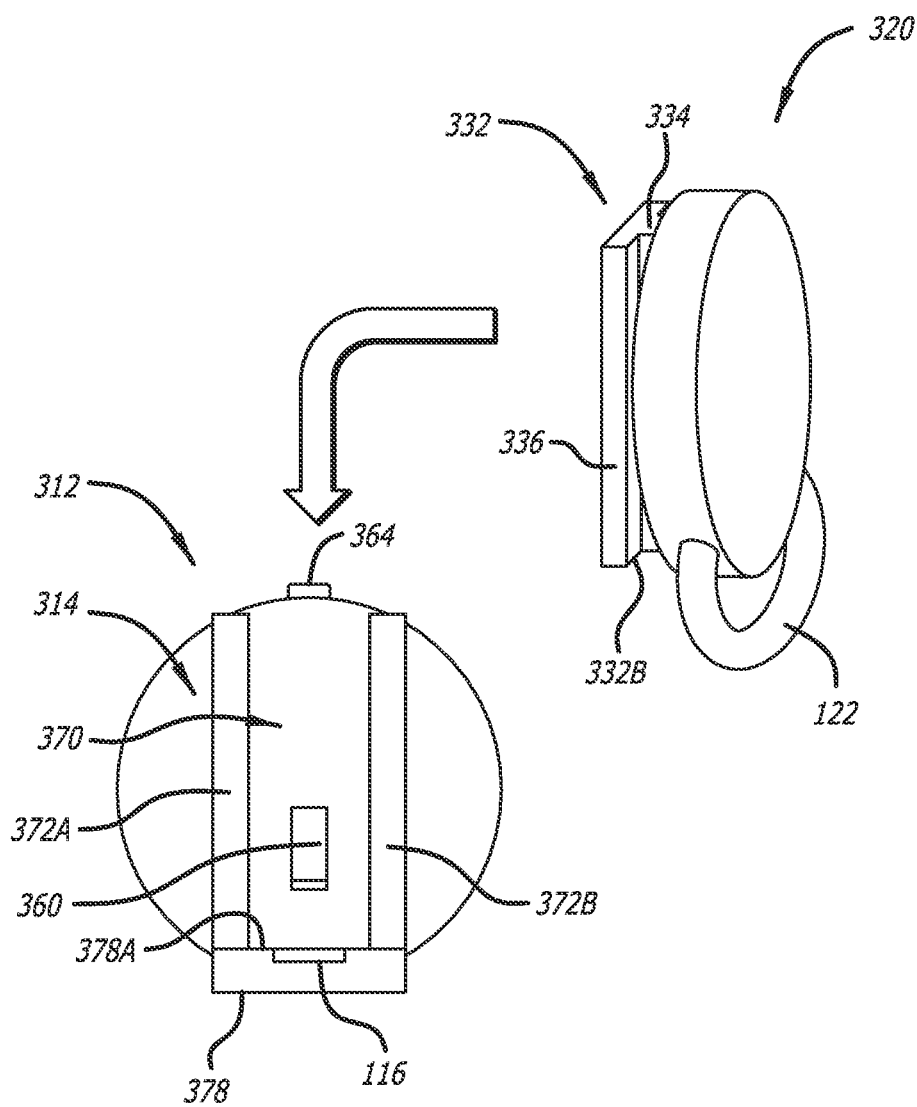
FIG. 5A shows a perspective view of a ring connector and a front view of a load cell interface, in accordance with embodiments disclosed herein.

In an embodiment, as shown in FIG. 4C, the shelf 140 can be angled such that a front-most edge 142 is disposed above a rear-most edge 144 of the shelf, along a vertical axis. Similarly, the ledge 240 can be angled such that a rear most edge 244 is disposed below a front-most edge 242, along a vertical axis. In an embodiment, one of the shelf 140 or the ledge 240 surface can be angled between 5° and 85° relative to a horizontal axis. In an embodiment, one of the shelf 140 or the ledge 240 surface can be angled between 30° and 45° relative to a horizontal axis. As such, any downward force applied to the ring connector 220 can bias the ledge 240 to further engage the shelf 140 more securely in a "French cleat" engagement.

While embodiments shown herein include a latch 232 disposed on the ring connector 220 and a carriage 270, shelf 140, and the like, disposed on the load cell 312, it will be appreciated that embodiments can include a latch 232 disposed on the load cell 212 and one of a carriage 270, shelf 140 or the like disposed on the ring connector 220 or combinations thereof.

FIGS. 5A-5D show an embodiment of a load cell 312 and a ring connector 320 that includes a channel locking mechanism 314. The ring connector 320 can include a track 332 that includes a post 334 extending from a rear surface of the ring connector 320 and a flange 336 extending laterally from the post 334 to define a "T-shaped" cross-sectional shape along a horizontal plane. The load cell 312 includes a channel 370 extending vertically and defined by a first rail 372A and a second rail 372B. The rails 372, can extend vertically along a front face of the load cell 312 and can each include a post 374 extending along a median plane from a front face of the load cell 312, and a lip 376 extending from the post 374 along a frontal plane, perpendicular to an axis of the post 374. The load cell 312 can further include a seat 378 disposed proximate a bottom end of the channel 370. The seat 378 defines an upper surface 378A extending horizontally from the load cell 312 front surface.

In an exemplary method of use the track 332 can engage the channel 370 to secure the ring connector 320 to load cell 312. A lower surface of the track can be aligned with a top edge of the channel 370. The flange 336 of the track 332 can engage a lip 376 of the channel 370. For example, as shown in FIG. 5B, a first flange 336A can engage a first lip 376A and a second flange 336B can engage a second lip 376B. The ring connector 320 can then be slid downwards along a vertical axis relative to the load cell 312 with the track 332 sliding vertically through the channel 370.

As shown in FIG. 5C, the track 332 can slide vertically downwards through the channel 370 until a bottom surface 332B of the track 332 engages a top surface 378A of the seat 378. The seat 378 prevents further downward vertical movement of the ring connector 320 relative to the load cell 312. Further, the seat 378 can be configured to support the weight of the ring connector 320 and the fluid collection system 150 coupled thereto.

In an embodiment, the seat 378 can include an electrical contact 116 disposed on the upper surface 378A thereof. Further, the track 332 can include an electrical contact 326 disposed on a lower surface 332B thereof. As such, with the track 332 engaged within the channel 370, the ring connector electrical contacts 326 can engage the load cell electrical contacts 116 to communicatively couple the ring connector 320 with the load cell 312, as described herein. Advantageously, the electrical contacts 116, 326 can engage along a vertical axis which is perpendicular to a surface 376A, 332B that the electrical contacts 116, 326 are disposed on. As such, the electrical contacts 116, 326 are prevented from sliding over each other which can cause wear and reduce the functional life of the system 100.

In an embodiment, the load cell 312 can include a pawl 360 configured to inhibit retrograde vertical movement of the track 332 relative to the channel 370. The pawl 360 can be hingedly coupled with the load cell 312 and can transition between an extended position that protrudes from a front surface of the load cell 312 (FIG. 5C) and a retracted position within the load cell 312 where the pawl 360 is aligned flush with a front surface of the load cell 312 (FIG. 5D). In an embodiment, the load cell 312 further includes a biasing member 366 configured to bias the pawl 360 to the extended position.

For example, the pawl 360 in the extended position can extend from the front surface load cell and can deflect into the load cell 312 as the rear face of the track 332 slides vertically downwards. As shown in FIG. 5C, with the track 332 seated within the channel 370, i.e. with the track lower surface 332B engaging the seat 378, the pawl 360 can align with a recess 362 disposed within the track 332. The pawl 360 can be biased to the extended position so as to engage the recess 362 when aligned therewith. Any vertical upwards movement can then be inhibited as the recess 362 of the track 332 abuts against a surface of the pawl 360.

In an embodiment, the load cell 312 can include a push-button actuator 364 coupled to the pawl 360 and configured to retract the pawl 360 into the load cell 312 when actuated. In an embodiment, to disengage the ring connector 320 from the load cell 312 a user can depress the actuator 364 to retract the pawl 360 into the load cell 312, allowing the track 332 to slide vertically upwards through the channel 370 to disengage the ring connector 320 from the load cell 312. As shown, the actuator 364 can be disposed on a top surface of the load cell 312 however it will be appreciated that the actuator 364 can be disposed on any outer surface of the load cell 312. As shown, the actuator 364 can be a push button, however it will be appreciated the actuator 364 can include a push button, switch, lever, rocker switch, slider, or similar device without limitation.

While embodiments shown herein include a track 332 disposed on the ring connector 320 and a channel 370, pawl 360, push button 364 disposed on the load cell 312, it will be appreciated that embodiments can include a track 332 disposed on the load cell 312 and one of a channel 370, pawl 360, push button 364 or the like disposed on the ring connector 320 or combinations thereof.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. An automatic fluid flow measuring system, comprising:
    a ring connector configured to be coupled to a fluid collection system and including a first electrical contact disposed on a first surface; and
    a load cell including a second electrical contact disposed on a second surface, the load cell configured to engage and retain the ring connector such that the first electrical contact engages the second electrical contact along an axis extending perpendicular to both the first surface and the second surface.

2. The automatic fluid flow measuring system according to claim 1, wherein one of the ring connector or the load cell includes a push-button actuator configured to releasably engage the load cell with the ring connector.

3. The automatic fluid flow measuring system according to claim 2, wherein the load cell includes a carriage defining the push-button actuator and slidable between a locked configuration and an unlocked configuration.

4. The automatic fluid flow measuring system according to claim 3, wherein the load cell includes a biasing member configured to bias the carriage towards the locked configuration.

5. The automatic fluid flow measuring system according to claim 3, wherein the push-button actuator is configured to transition the carriage from the locked configuration to the unlocked configuration.

6. The automatic fluid flow measuring system according to claim 3, wherein the carriage includes an aperture configured to receive a latch in the unlocked configuration and retain the latch in the locked configuration, the latch extending from a rear surface of the ring connector.

7. The automatic fluid flow measuring system according to claim 6, wherein a surface of the latch engages the load cell to transfer a force from the ring connector to the load cell.

8. The automatic fluid flow measuring system according to claim 2, wherein the load cell includes a shelf extending horizontally across a portion of a front face of the load cell, and configured to engage the ring connector to receive a force from the ring connector to the load cell.

9. The automatic fluid flow measuring system according to claim 8, wherein the load cell and the ring connector engage using a French cleat mechanism.

10. The automatic fluid flow measuring system according to claim 2, wherein the load cell includes a first rail and a second rail defining a channel and configured to slidably engage a track in a first direction, the track extending from a rear surface of the ring connector.

11. The automatic fluid flow measuring system according to claim 10, wherein the load cell includes a pawl configured to engage a recess disposed on the ring connector, the pawl configured to inhibit movement of the track within the channel in a second direction.

12. The automatic fluid flow measuring system according to claim 11, wherein the push-button actuator is configured to retract the pawl to allow movement of the track in the second direction.

13. The automatic fluid flow measuring system according to claim 10, wherein the track defines a T-shaped horizontal cross-section and the channel is configured to slidably receive the track along a vertical axis.

14. The automatic fluid flow measuring system according to claim 10, wherein the load cell includes a seat configured to engage the ring connector and to transfer a force from the ring connector to the load cell.

15. The automatic fluid flow measuring system according to claim 14, wherein a lower surface of the ring connector defines the first surface and a top surface of the seat defines the second surface.

16. A method of measuring a fluid flow, comprising:
actuating a push button actuator disposed on a load cell, the load cell configured to releasably engage a ring connector coupled to a fluid collection system;
transitioning a carriage from a locked configuration to an unlocked configuration;
urging a latch through an aperture of the carriage, the latch extending from a rear surface of the ring connector;
transitioning the carriage from the unlocked configuration to the locked configuration to retain the latch within the aperture;
detecting a force applied to the load cell by the ring connector to determine a fluid volume disposed within the fluid collection system; and
detecting a change in the force over time to determine a fluid flow.

17. The method according to claim 16, further including engaging a first electrical contact disposed on the ring connector, with a second electrical contact disposed on the load cell to communicatively couple the ring connector to the load cell.

18. The method according to claim 16, wherein the load cell includes a biasing member configured to bias the carriage to the locked configuration.

19. The method according to claim 16, wherein the load cell includes a shelf extending horizontally and configured to engage the ring connector to transfer the force from the ring connector to the load cell.

20. The method according to claim 16, wherein the load cell includes a French cleat configured to engage the ring connector to transfer the force from the ring connector to the load cell.

21. The method according to claim 16, wherein the ring connector includes logic configured to store one of fluid flow information, system information, or patient information thereon.

22. A method of measuring a fluid volume, comprising:
providing a load cell including a channel configured to slidably engage a track extending from a ring connector, the ring connector coupled to a fluid collection system;
sliding the track through the channel in a first direction until a surface of the ring connector engages a seat extending from the load cell;
transferring a force from the ring connector to the load cell; and
detecting a change in the force over time to determine a fluid flow.

23. The method according to claim 22, further including engaging a first electrical contact disposed on the ring connector, with a second electrical contact disposed on the seat of the load cell, to communicatively couple the ring connector to the load cell.

24. The method according to claim 23, wherein the ring connector includes logic configured to store one of fluid flow information, system information, or patient information thereon.

25. The method according to claim 22, further including engaging a pawl, extending from the load cell, with a recess disposed on the ring connector to inhibit movement of the track through the channel in a second direction, opposite the first direction.

26. The method according to claim 25, further including actuating a push-button to retract the pawl from the recess to allow the track to slide through the channel in the second direction.

27. The method according to claim 25, wherein the load cell includes a biasing member configured to bias the pawl to an extending position.

* * * * *